(12) United States Patent
Engelhard

(10) Patent No.: US 9,162,903 B2
(45) Date of Patent: Oct. 20, 2015

(54) PHOTO-CATALYZING FLUID MOBILIZING SYSTEM AND METHOD

(75) Inventor: Rolf Engelhard, Prescott, AZ (US)

(73) Assignee: Blutec, LLC, Las Vegas, NV (US)

( * ) Notice: Subject to any disclaimer, the term of this patent is extended or adjusted under 35 U.S.C. 154(b) by 1166 days.

(21) Appl. No.: 13/076,367

(22) Filed: Mar. 30, 2011

(65) Prior Publication Data

US 2011/0240566 A1    Oct. 6, 2011

Related U.S. Application Data

(60) Provisional application No. 61/319,215, filed on Mar. 30, 2010.

(51) Int. Cl.
| | |
|---|---|
| C02F 1/32 | (2006.01) |
| B01D 53/88 | (2006.01) |
| B01J 19/12 | (2006.01) |
| B01J 19/18 | (2006.01) |
| C02F 1/72 | (2006.01) |

(52) U.S. Cl.
CPC .............. *C02F 1/325* (2013.01); *B01D 53/885* (2013.01); *B01J 19/123* (2013.01); *B01J 19/18* (2013.01); *C02F 1/725* (2013.01); *B01D 2255/20707* (2013.01); *B01D 2255/802* (2013.01); *B01D 2257/708* (2013.01); *B01D 2257/91* (2013.01); *B01D 2259/4508* (2013.01); *B01D 2259/4533* (2013.01); *B01D 2259/804* (2013.01); *B01J 2219/0877* (2013.01); *B01J 2219/0892* (2013.01); *C02F 2201/326* (2013.01); *C02F 2201/3227* (2013.01); *C02F 2201/3228* (2013.01); *C02F 2305/10* (2013.01); *Y02W 10/37* (2015.05)

(58) Field of Classification Search
USPC ................. 210/739, 748.01, 748.04, 748.1, 210/748.11, 748.14, 748.16, 749, 143, 153, 210/194, 198.1, 252; 422/20, 22, 24, 143, 422/186, 186.3; 250/432 R
See application file for complete search history.

(56) References Cited

U.S. PATENT DOCUMENTS

| | | | | |
|---|---|---|---|---|
| 4,422,824 | A * | 12/1983 | Eisenhardt, Jr. | ................... 416/5 |
| 6,303,087 | B1 * | 10/2001 | Wedekamp | ................ 422/186.3 |
| 6,365,113 | B1 * | 4/2002 | Roberts | ....................... 422/186.3 |
| 7,695,675 | B2 * | 4/2010 | Kaiser et al. | ..................... 422/24 |
| 7,972,564 | B2 * | 7/2011 | Chan | ............................. 422/120 |
| 2003/0143133 | A1 | 7/2003 | Liu | |
| 2003/0155524 | A1 | 8/2003 | McDonald et al. | |
| 2008/0213129 | A1 * | 9/2008 | van der Pol et al. | ............ 422/24 |
| 2009/0285727 | A1 | 11/2009 | Levy | |

FOREIGN PATENT DOCUMENTS

| | | | | |
|---|---|---|---|---|
| CN | 002531297 Y | * | 1/2003 | ................ F24F 3/16 |
| WO | WO 2008/117962 | | 10/2008 | |

* cited by examiner

*Primary Examiner* — Walter D Griffin
*Assistant Examiner* — Cameron J Allen
(74) *Attorney, Agent, or Firm* — Mintz Levin Cohn Ferris Glovsky and Popeo, P.C.

(57) ABSTRACT

A photo-catalyzing fluid mobilizing system and method are disclosed. A chamber has a power source. A fluid mobilizer is mounted in the chamber and connected with the power source to mobilize a fluid through the chamber. The fluid mobilizer includes one or more fan blades that are coated with a photo catalyst. A UV light source is mounted in the chamber proximate the fluid mobilizer and connected with the power source to catalyze the photo catalyst coating the blades to purifier the fluid being mobilized thereover.

4 Claims, 3 Drawing Sheets

PHOTO-CATALYZING FLUID MOBILIZING SYSTEM AND METHOD

CROSS REFERENCE TO RELATED APPLICATIONS

This application claims the benefit of priority under 35 U.S.C. §119 to U.S. Provisional Patent Application Ser. No. 61/319,215, filed on Mar. 30, 2010, entitled, "PHOTO-CATALYZING FLUID MOBILIZING SYSTEM AND METHOD", the entire disclosures of which is incorporated by reference herein.

BACKGROUND

One of the most effective methods for air purification is photo catalysis. Photo catalysis occurs when a photo catalyst is irradiated by ultra-violet light in the UV-A, UV-B and UV-C range. In a typical application, a UV-irradiated surface is coated with a photo catalytic material such as titanium dioxide. Photo catalysis occurs on a very thin boundary layer above the surface of the photo catalyst. This presents one of the limitations of photo catalysis for air or water purification, since it is difficult to bring all the fluid to be purified to the UV-irradiated photo catalyst. This invention addresses this limitation and presents a novel method to move a fluid past an irradiated photo catalyst.

Photo-catalysis is generally defined as "acceleration by the presence of a catalyst". A catalyst does not change in itself or being consumed in the chemical reaction. This definition includes photosensitization, a process by which a photochemical alteration occurs in one molecular entity as a result of initial absorption of radiation by another molecular entity called the photosensitized. Chlorophyll of plants is a type of photo catalyst. Compared to photosynthesis, in which chlorophyll captures sunlight to turn water and carbon dioxide into oxygen and glucose, photo catalysis with light and water creates a strong oxidation agent to break down any organic matter to carbon dioxide and water.

Photo catalysis is effective for sterilizing, deodorizing, and purifying fluids such as air or water. However, conventional fluid purification systems do not take advantage of photo catalysts.

SUMMARY

This document presents a system and method for photo-catalyzing and mobilizing a fluid, such as air or water.

According to one aspect, a photo-catalyzing fluid mobilizing system includes a chamber having a power source, and a fluid mobilizer mounted in the chamber and connected with the power source. The fluid mobilizer mobilizes a fluid through the chamber using one or more fan blades that are coated with a photo catalyst. The system further includes a UV light source mounted in the chamber proximate the fluid mobilizer and connected with the power source to catalyze the photo catalyst coating the blades to purifier the fluid being mobilized thereover.

According to another aspect, a photo-catalyzing fluid mobilizing method includes the steps of mobilizing, using a fluid mobilizer, a fluid through a chamber and over at least one fan blade of the fluid mobilizer, the fan blade being coated with a photo catalyst. The method further includes the steps of irradiating the fan blade with UV light to catalyze the photo catalyst, and purifying the fluid being mobilized through the chamber with the catalyzed photo catalyst.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

Figure 1:
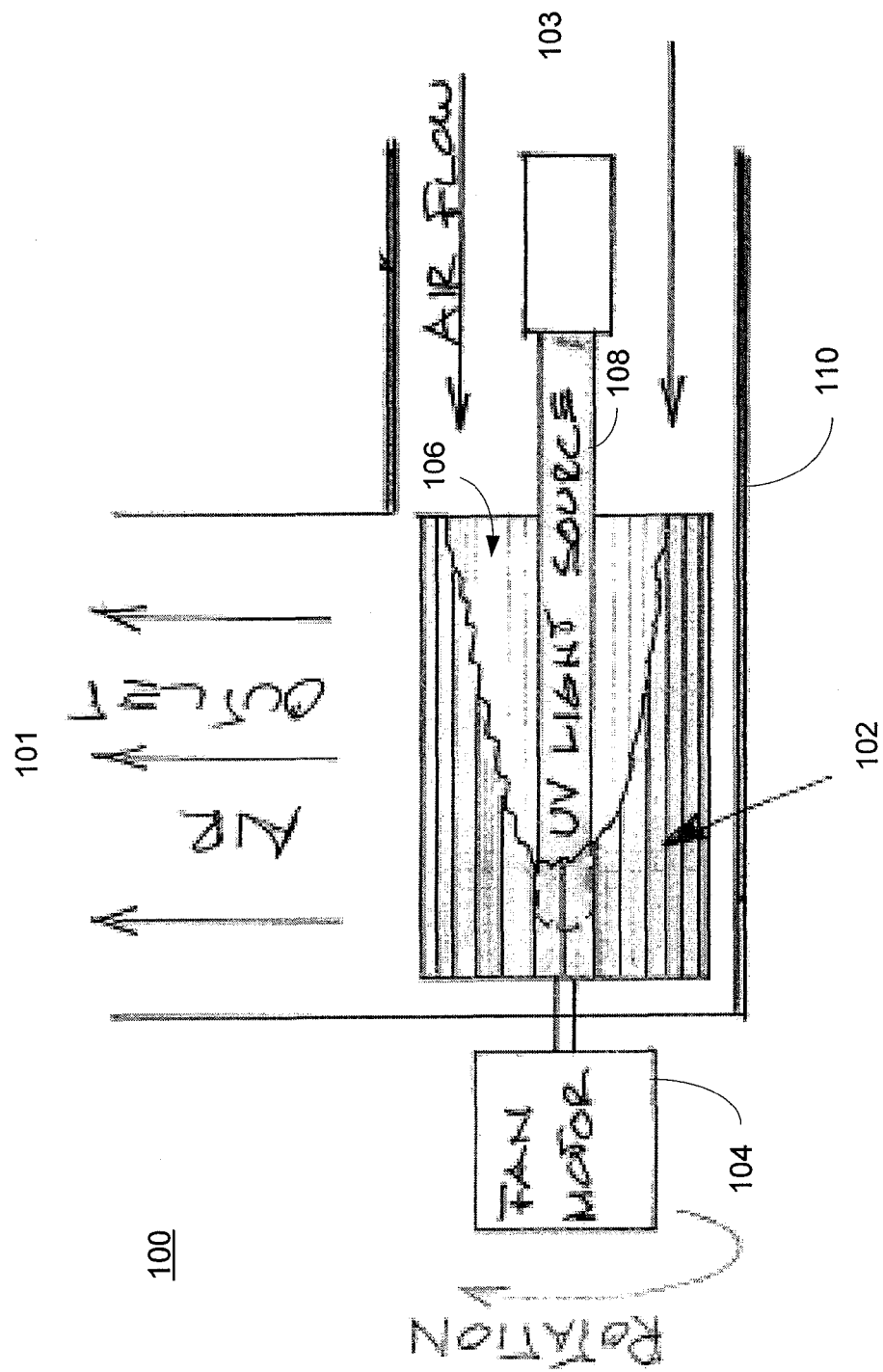
FIG. 1 is a photo-catalyst fluid purification system using a centrifugal or radial fan having a photo-catalytic coating.

This document describes a high intensity air purifier, a super oxidation purifier, and a controller for controlling operation of any of various purification systems described herein.

When a photo catalyst such as titanium dioxide ($T_1O_2$) absorbs Ultraviolet (UV) radiation from sunlight or other illuminated light source (fluorescent lamps), it will produce pairs of electrons and holes. The electron of the valence band of titanium dioxide becomes excited when illuminated by light. The excess energy of this excited electron promoted the electron to the conduction band of titanium dioxide therefore creating the negative-electron (e−) and positive-hole (h+) pair. This stage is referred as the semiconductor's 'photo-excitation' state. The energy difference between the valence band and conduction band is known as the "Band Gap." Wavelength of the light necessary for photo-excitation is: 1240 (Planck's constant, h)/3.2 ev (band gap energy)=388 nm.

For sterilization, a photo catalyst not only kills bacteria cells, but also decomposes the cell itself. A titanium dioxide photo catalyst has been found to be more effective than any other antibacterial agent, because the photo catalytic reaction works even when there are cells covering the surface and while the bacteria are actively propagating. The end toxin produced at the death of cell is also expected to be decomposed by the photo catalytic action. Titanium dioxide does not deteriorate and it shows a long-term antibacterial effect. Generally speaking, disinfections by titanium oxide are three times stronger than chlorine, and 1.5 times stronger than ozone.

On the deodorizing application, the hydroxyl radicals accelerate the breakdown of any Volatile Organic Compounds or VOCs by destroying the molecular bonds. This will help combine the organic gases to form a single molecule that is not harmful to humans thus enhance the air cleaning efficiency. Some of the examples of odor molecules are: tobacco odor, formaldehyde, nitrogen dioxide, urine and fecal odor, gasoline, and many other hydrocarbon molecules in the atmosphere. An air purifier with $T_1O_2$ can prevent smoke and soil, pollen, bacteria, virus and harmful gas as well as seize the free bacteria in the air by filtering percentage of 99.9% with the help of the highly oxidizing effect of photo catalyst.

For air purification, the photo catalytic reactivity of titanium oxides can be applied for the reduction or elimination of polluted compounds in air such as NOx, cigarette smoke, as well as volatile compounds arising from various construction materials. Also, high photo catalytic reactivity can be applied to protect lamp-houses and walls in tunneling, as well as to prevent white tents from becoming sooty and dark. Atmospheric constituents such as chlorofluorocarbons (CFCs) and CFC substitutes, greenhouses gases, and nitrogenous and sulfurous compounds undergo photochemical reactions either directly or indirectly in the presence of sunlight. In a polluted area, these pollutants can eventually be removed.

For water purification, a photo catalyst coupled with UV lights can oxidize organic pollutants into nontoxic materials, such as $CO_2$ and water, and can disinfect certain bacteria. This technology is very effective at removing further hazardous organic compounds (TOCs) and at killing a variety of bacteria and some viruses in the secondary wastewater treatment. Photo catalytic detoxification systems have been demonstrated to effectively kill fecal coli form bacteria in secondary wastewater treatment.

With reference to FIG. 1, a photo-catalytic fan 100 includes an inlet 101, an outlet 103, and an air fan/blower that has a fluid mobilizer 102, which can be a rotor, blower wheel, fan, propeller or impeller, to mobilize a fluid such as air or water. The fluid mobilizer 102 can be operated by a fan motor 104. The fluid mobilizer 102 is coated with a photo catalyst 106, which can be any material that produces a photo catalytic reaction when irradiated by ultra-violet (UV) light. One such photo catalyst is titanium dioxide. The fluid mobilizer serves several different functions: it moves the fluid that is to be purified; and it acts as the substrate for the photo catalytic material. Fans, rotor blades, impellers characteristically have a large surface area, which makes them ideally suited as the substrate for the photo catalyst.

The photo-catalytic fan 100 further includes an ultra-violet light source 108 that irradiates the photo catalytic surfaces of the fan/blower blades of the fluid mobilizer 102. The ultra-violet light source 108 can be one or more ultra-violet lamps, which can be constructed in many different shapes including bulb-shaped, cylindrical, u-shaped, circular and spot lamps such as recently developed LEDs or UV lasers. As such, lamp shapes can be chosen for each different type of fluid mobilizer 102, to ideally irradiate the maximum surface area of the photo catalyst 106.

Figure 2:
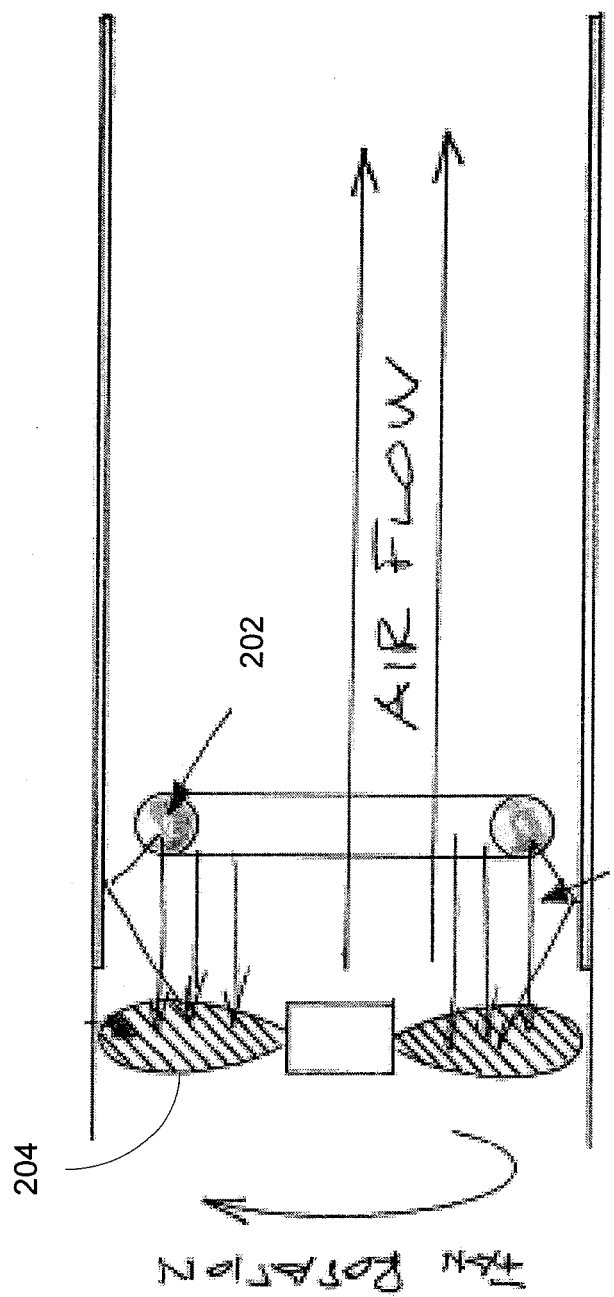
FIG. 2 is a photo-catalyst fluid purification system using a propeller or impeller-type fan having a photo-catalytic coating.
Figure 3:
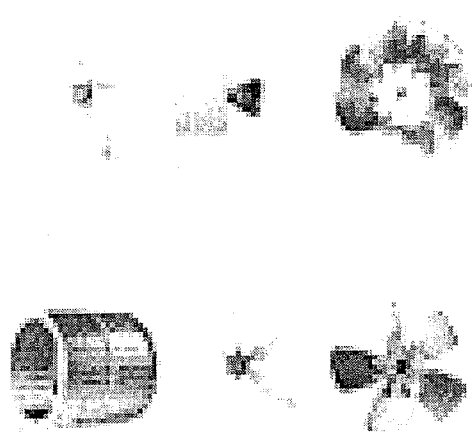
FIG. 3 illustrates alternative fan configurations for a fluid mobilizer.

FIGS. 2 and 3, along with FIG. 1, show a number of possible fan/lamp combinations. FIG. 2 shows a circular ultra-violet lamp 202 that provides the ultra-violet light source, and where a fan blade 204 is coated with a photo catalyst. In one preferred implementation, the ultra-violet lamp 202 is ring-shaped and circumscribes an inner surface of the chamber that contains the ultra-violet lamp 202. FIG. 3 illustrates alternative fan configurations for a fluid mobilizer.

The photo-catalytic fan 100 further includes a chamber 110 that contains the fluid mobilizer 102 and the ultra-violet light source 108. The chamber may include a UV-reflective surface on the interior walls of the part of the chamber that houses the fan/blower and the UV light source 108. The reflective surface is preferably be a lambertian reflector that reflects a very high percentage of the UV light that strikes the interior wall of the chamber 110, and directs this light toward the photo catalytic surfaces of the fan/blower blades of the fluid mobilizer 102.

The photo-catalytic fan 100 is suitable for any types of fluids, including air or water. In a water purification device, the shape of the propeller, impeller, rotor or fan blades will have a different shape or pitch than the air blades and will rotate at a speed that is appropriate to move or mobilize water. The strength of the UV light source is also adjustable so as to adjust for the reflective and refractive qualities of water. In some implementations, a single device can be made for both water and air, and include a setting for either mode. The setting will adjust the shape or pitch of the fan blades, rotation speed of the fan, and possibly the light strength of the UV light source.

The photo-catalytic fan 100 can further include filters or flow directors within the chamber, for filtering out large particles and to direct the air properly toward the UV light source, respectively. The chamber can be a hollow cylinder, and can be made of any suitable rigid material, such as plastic, nylon, stainless steel, aluminum, or the like.

Although a few embodiments have been described in detail above, other modifications are possible. Other embodiments may be within the scope of the following claims.

The invention claimed is:

1. A system for mobilizing and photo-catalyzing a fluid, the system comprising:
    a chamber having a power source;
    a fluid mobilizer mounted in the chamber and connected with the power source to mobilize a fluid through the chamber, the fluid mobilizer including one or more longitudinal fan blades that are coated with a photo catalyst; and
    an ultra-violet (UV) light source mounted in the chamber proximate the fluid mobilizer and connected with the power source to catalyze the photo catalyst coating the blades to purify the fluid being mobilized thereover, the UV light source including one or more UV lamps, wherein at least one of the one or more UV lamps is disposed within the longitudinal fan blades, such that the longitudinal fan blades rotate about the at least one of the one or more UV lamps and form a passageway between the at least one of the one or more UV lamps and an inner surface of the one or more longitudinal fan blades, and wherein the fluid is mobilized through the passageway between the at least one of the one or more UV lamps and the inner surface of the one or more longitudinal fan blades.

2. The system in accordance with claim 1, wherein the fluid is water, and wherein a strength of the UV light source is adjustable to adapt to the reflective and refractive qualities of the water.

3. The system in accordance with claim 1, wherein an interior surface of the chamber includes a UV reflective surface.

4. The system in accordance with claim 1, wherein the interior surface of the at least one of the one or more longitudinal fan blades includes a UV reflective surface.

* * * * *